United States Patent [19]

Müller

[11] Patent Number: 5,126,244
[45] Date of Patent: Jun. 30, 1992

[54] DETERMINATION OF ANTIGENS

[75] Inventor: Hanne-Lene Müller, Oberwil, Switzerland

[73] Assignee: Hoffmann-La Roche Inc., Nutley, N.J.

[21] Appl. No.: 272,288

[22] Filed: Nov. 17, 1988

[30] Foreign Application Priority Data

Nov. 27, 1987 [CH] Switzerland ............ 4616/87

[51] Int. Cl.$^5$ .............. G01N 33/569; C12N 1/06
[52] U.S. Cl. ..................... 435/7.31; 435/7.32; 435/7.34; 435/7.37; 435/961; 435/259; 436/175; 536/127
[58] Field of Search .............. 435/7, 30, 34, 38, 101, 435/240, 25, 803, 849, 863, 885, 7.32-7.37, 961, 7.31, 259; 436/501, 536, 543, 63, 174; 536/127, 123, 114

[56] References Cited

U.S. PATENT DOCUMENTS 3,148,120 9/1964 Westphal .
4,029,762 6/1977 Galanos et al. ............ 424/92
4,285,936 8/1981 Pier et al. .
4,755,382 7/1988 Flaherty ............... 424/92

FOREIGN PATENT DOCUMENTS 1073694 6/1967 United Kingdom .

OTHER PUBLICATIONS

Palmer et al., *Science* 92(2381):155, 1940.
Mozkowitz et al., *J. Bacteriol* 91(6):2200, 1966.
Westphal et al., in Meth. Carbohydrate Chem. Whistler et al., eds. Academic Press: New York, 1965.
Behling et al. *Infection and Immunity* 26(2): 580, 1979.
Perry et al. *Canadian J. Biochem.* 53(4):623, 1975.
Hamada et al. *Microbiol. Immunol.* 28(9):1009, 1984.
Rodahl et al. *Acta path. Microbiol. Immunol. Scand. Sect. C.* 92:247, 1984.
Munford, R. S., et al. *J. Clin. Invest.*, vol. 70, Oct. 1982, pp. 877-888.
Rodahl, E. et al., Biological Abstracts, vol. 79(9), No. 58668, 1984.
Hamada, S. et al., Biological Abstracts, vol. 79(3), No. 22113, 1984.
Behling, V. H. et al., Biological Abstracts, vol. 69(7), No. 44923, 1979.
Fine, D. H. et al., Biological Abstracts, vol. 66(11), No. 65567, 1978.
Carlsson, H. E. et al., Biological Abstracts, vol. 62(10), No. 55606, 1976.
Westphal et al., *Z. Naturforsch* 76:148 (1952).

*Primary Examiner*—Esther L. Kepplinger
*Assistant Examiner*—Carol E. Bidwell
*Attorney, Agent, or Firm*—George M. Gould; William H. Epstein; Bruce A. Pokras

[57] ABSTRACT

A method for the liberation of polysaccharide antigens from bacteria or fungi in biological probes or in grown cultures of these probes is described. In the majority of cases such a liberation is necessary in order that subsequently the polysaccharide antigens can be determined immunologically in a manner known per se. This liberation is effected by treating the biological probe or the grown culture with an aqueous phenol solution. A 1-10% phenol solution is conveniently used, with a 2-5% phenol solution being preferred and a 2% phenol solution being especially preferred. The phenol solution is allowed to act on the probe or culture for 5-30%, preferably 15, minutes. No extraction is necessary for the subsequent immunological determination of the polysaccharides.

12 Claims, No Drawings

DETERMINATION OF ANTIGENS

TECHNICAL FIELD

The instant invention is directed to a pre-treatment to liberate polysaccharide antigens from biological probes in order to enable the use of these antigens in immunological determinations.

BACKGROUND OF THE INVENTION

In practice, diverse methods are used to liberate the antigens, namely heating to 100° C., an enzymatic treatment at 37° C. or an extraction with sodium nitrite in two operational steps.

Another known procedure for the extraction of these antigens is a treatment with high-percentage phenol, e.g. 90% saturated phenol (90% phenol/10% water) at a temperature of 60° C.

The heating to 100° C. as well as the enzymatic treatment for the antigen liberation can not be effected in the presence of specific antibodies, since these are denatured. A re-pipetting must also be effected. The same applies in the case of a high-percentage phenol extraction, which additionally requires a centrifugation. The extraction with sodium nitrite involves two separate reagents and subsequent treatment with Tris buffer.

This means that these known procedures are extremely circumstantial and time consuming and are therefore anything but conformable in practice.

SUMMARY OF THE INVENTION

In the scope of the present invention there has now been found a method for the liberation of polysaccharide antigens from bacteria or fungi in biological probes or in grown cultures of these probes for the subsequent immunological determination of these antigens, which method comprises treating the biological probe or the grown culture with an aqueous phenol solution.

DETAILED DESCRIPTION

A 1-10% aqueous phenol solution can be used in the method in accordance with the present invention, with a 2-5% aqueous phenol solution being preferred and a 2% aqueous phenol solution being especially preferred.

Blood, serum, plasma, urine, faeces or sputum are suitable biological probes for the method in accordance with the present invention.

It has been found that in accordance with the method provided by the invention one part of aqueous phenol solution is used per 5 parts of biological probe or culture.

In the method in accordance with the present invention the aqueous phenol solution can be allowed to act on the probe or culture for 5-30 minutes, preferably for 15 minutes.

The temperature used in the pre-treatment is not critical. The pre-treatment is conveniently effected between 15° C. and up to just before the boiling point of the reaction mixture, with room temperature being especially preferred.

No extraction is necessary for the subsequent immunological determination of the polysaccharide antigens, which means that the immunological detection method can be carried out in the medium in which the liberation of the antigens has been effected.

The aforementioned immunological detection method can be effected in a manner known per se, especially according to the so-called ELISA technique.

The method in accordance with the present invention is excellently suited to the detection of polysaccharide antigens from streptococci, especially from *Streptococcus pneumoniae*, from mycobacteria, especially *Mycobacterium tuberculosis*, or from enterobacteriaceae, especially *Escherichia coli*.

In the scope of the present invention it has furthermore been found that the method in accordance with the invention not only requires less intensive work, but in most cases also offers an improved sensitivity with respect to the determination of the polysaccharide antigens.

The following Examples illustrate the invention.

EXAMPLE 1

A) ELISA test methodology

A.1.) Qualitative determination of mycobacteria antigens in culture-grown bacteria and body fluids with mycobacteria antibodies from rabbits.

Into each of the requisite number of test tubes (10×25 mm) there is pipetted 0.25 ml of probe material (bacterial suspension, serum, liquified sputum, urine), and thereto there is added 0.05 ml of the reaction reagent (phenol or $NaNO_2$+acetic acid+Tris buffer) or $H_2O$. After adding an anti-mycobacteria-sensitized polystyrene bead ($\phi$=6.5 mm) to each test tube the batch is incubated at room temperature for 30 minutes. Subsequently, without a washing operation, 0.25 ml of rabbit-anti-mycobacteria-peroxidase conjugate (0.1M tris-hydroxymethyl-aminomethane, pH 7.0 inactivated with 20% foetal calf serum, 0.05% Tween 20 and 3 μg/ml of rabbit-anti-mycobacteria-peroxidase conjugate) is added. Thereafter, the batch is incubated at room temperature for 4 h. After the incubation period the polystyrene beads are washed twice in an EIA washer <Roche> with in each case 5 ml of twice-dist. water. Thereafter, there is added to each of the test tubes 0.25 ml of substrate buffer in order to determine the activity of the peroxidase (0.1 mol/l potassium citrate buffer of pH 5.2 with 6 mmol/l $H_2O_2$ and 20 mmol/l o-phenylenediamine) and incubation is carried out at room temperature for 15 min. In order to stop the peroxidative activity and to intensify the colour intensity 1.0 ml of 1N $H_2SO_4$ is added and the extinction at the wavelength 492 nm is measured photometrically within 30 minutes, e.g. with the EIA photometer <Roche>.

A.2) Qualitative determination of pneumococci antigens to culture-grown bacteria and body fluids with pneumococci antibodies from rabbits.

Into each of the requisite number of test tubes (10×25 mm) there is pipetted 0.25 ml of probe material (bacterial suspension or serum, liquified sputum, urine) or PBS (blank) and thereto there is added 0.05 ml of the reaction reagent (phenol or $NaNO_2$+acetic acid+Tris buffer) or $H_2O$. After adding an anti-pneumococci-sensitized polystyrene bead ($\phi$=6.5 mm) to each test tube the batch is incubated at room temperature for 15 minutes. Subsequently, without a washing operation, 0.25 ml of rabbit-anti-pneumococci-peroxidase conjugate (0.1M tris-hydroxymethyl-aminomethane, pH 7.0 inactivated with 20% foetal calf serum, 0.05% Tween 80 and 0.7 μg/ml rabbit-anti-pneumococci-peroxidase conjugate) is added. Thereafter, the batch is incubated at room temperature for 60 minutes. After the incubation period the polystyrene beads are washed twice in an EIA washer <Roche> with in each case 5 ml of twice-dist. water. Thereafter, there is added to each of the test tubes 0.25 ml of substrate buffer in order to determine the activity of the peroxidase (80 mmol/l potassium citrate buffer pH 4.25 with 1.6 mmol/l $H_2O_2$ and 1 mmol/l 3,3',5,5'-tetramethylbenzidine in 13.4% DMSO with 6.6% 2-propanol) and the test tubes are held at room temperature for 5 minutes. In order to stop the After incubation for about 1 week the colonies were washed with physiological NaCl solution and adjusted to a McFarland density of about 0.5.

The suspension was divided into 5 equal parts and subjected to the various pre-treatments: thereafter in each case a one-step enzyme immunoassay was carried out. The performance of the test was effected in accordance with Example 1.

The following results were obtained:

| | *Mycobacterium Calmette* Guerin (BCG) | | | |
|---|---|---|---|---|
| | Treatment period | | | |
| | 15 minutes | | 30 minutes | |
| | Calculation | | | |
| Type of treatment | OD probe − OD blank | $\frac{\text{OD probe}}{\text{OD blank}}$ | OD probe − OD blank | $\frac{\text{OD probe}}{\text{OD blank}}$ |
| 250 μl probe + 50 μl $H_2O$ | 0.794 | 5.1 | 0.842 | 5.8 |
| 250 μl probe + 50 μl 1% phenol | 1.145 | 7.4 | 1.186 | 8.2 |
| 250 μl probe + 50 μl 2% phenol | 1.608 | 9.8 | 1.731 | 10.8 |
| 250 μl probe + 50 μl 2.5% phenol | 1.612 | 11.2 | 1.764 | 12.3 |
| 250 μl probe + 300 μl $H_2O$ | n.d. | n.d. | 0.156 | 2.0 |
| 250 μl probe + 100 μl $NaNO_2$ 1M + 100 μl acetic acid 1M + 100 μl Tris buffer* | n.d. | n.d. | 0.130 | 1.8 |

*The Tris buffer was added in each case 15 minutes after the reagents had taken effect.

peroxidative activity and to intensify the colour intensity there is added 1.0 ml of 1N $H_2SO_4$ and the extinction at the wavelength 450 nm is measured photometrically within 30 minutes, e.g. with the EIA photometer <Roche>.

A.3.) Qualitative determination of *E. coli* antigens in culture-grown bacteria and body fluids with *E. coli* antibodies from rabbits Into each of the requisite number of test tubes (10×25 mm) there is pipetted 0.25 ml of probe material (bacterial suspension or serum, urine) or PBS (blank), and thereto there is added 0.05 ml of the reaction reagent (phenol or $NaNO_2$+acetic acid+Tris buffer) or PBS. After adding an anti-*E. coli*-sensitized polystyrene bead ($\phi$=6.5 mm) to each test tube the batch is incubated at room temperature for 15 minutes. Subsequently, without a washing operation, 0.25 ml of rabbit-anti-*E. coli*-peroxidase conjugate (0.1M trishydroxymethylaminomethane, pH 7.0 inactivated with 20% foetal calf serum, 0.05% Tween 20 and 1 μg/ml rabbit-anti-*E. coli*-peroxidase conjugate) is added. Thereafter, the batch is incubated at RT for 30 minutes. After the incubation period the polystyrene beads are washed twice in an EIA washer <Roche> with in each case 5 ml of twice-dist. water. Thereafter, there is added to each of the test tubes 0.25 ml of substrate buffer in order to determine the activity of the peroxidase (0.1 mol/l potassium citrate buffer of pH 5.2 with 6 mmol/l $H_2O_2$ and 20 mmol/l o-phenylenediamine) and incubation is carried out at room temperature for 15 min. In order to stop the peroxidative activity and to intensify the colour intensity 1.0 ml of (1N) $H_2SO_4$ is added and the extinction at the wavelength 492 nm is measured photometrically within 30 minutes, e.g. with the EIA photometer <Roche>.

EXAMPLE 2

B. Liberation of antigens from culture-grown bacteria

B.1.) Mycobacterium Calmette Guerin (BCG).

Several test tubes containing Middlebrook agar of the firm Difco were inoculated from a freshly opened ampoule of BCG vaccine from the Serum Institute Berne.

B.2.) Pneumococci

Streptococcus pneumoniae was grown overnight on blood plates. Thereafter, a suspension of the colonies in physiological NaCl solution having the McFarland density 1.0 was prepared. The suspension was divided into 5 equal parts and the various pre-treatments were carried out. The one-step enzyme immunoassay was subsequently carried out. The performance of the test was effected as in Example 1.

The following results were obtained:

| | Pneumococci - positive sputum | |
|---|---|---|
| | Treatment period 30 minutes RT | |
| | Calculation | |
| Type of treatment | OD probe − OD blank | $\frac{\text{OD probe}}{\text{OD blank}}$ |
| 250 μl probe + 50 μl $H_2O$ | 0.028 | 9.2 |
| 250 μl probe + 50 μl 5% phenol | 2.261 | 26.1 |
| 250 μl probe + 50 μl $H_2O$ 100° C. | 1.232 | 13.7 |
| 250 μl probe + 1 gH $NaNO_2$ 1M + 1 gH acetic acid 1M + 1 gH Tris buffer* | 1.912 | 18.9 |

*The Tris buffer was added in each case 15 minutes after the reagents had taken effect.

B.3.) *Escherichia coli*

*E. coli* ATCC 19110 was grown overnight on blood plates. Thereafter a suspension of the colonies in physiological NaCl solution with the McFarland density 1.0 was prepared. The suspension was divided into 4 equal parts and subjected to the various pre-treatments. Thereafter, in each case a one-step enzyme immunoassay was carried out. For the performance of the test see under methodology.

The following results were obtained:

| Type of treatment | Treatment period 15 minutes RT Calculation | |
|---|---|---|
| | OD probe − OD blank | OD probe / OD blank |
| 250 μl probe + 50 μl H₂O | 2.166 | 12.2 |
| 250 μl probe + 50 μl 2% phenol | 1.950 | 11.5 |
| 250 μl probe + 50 μl 5% phenol | 2.096 | 14.8 |
| 250 μl probe + 50 μl H₂O 100° C. | 1.841 | 10.5 |
| 250 μl probe + 60 μl reagent mix (NaNO₂, acetic acid, Tris buffer*) | 2.100 | 11.3 |

*The Tris buffer was added in each case 15 minutes after the reagents had taken effect.

EXAMPLE 3

C. Liberation of antigens in infectious investigational material

The further investigations were carried out on material from patients. The one-step EIA test was carried out in accordance with Example 1. The pre-treatments were effected according to the attached Scheme.

Scheme of parallel investigations with different pre-treatments:

| Batch | None | | 100° C. 15 min | | Phenol 2% | | Phenol 5% | | Reagent mixture | |
|---|---|---|---|---|---|---|---|---|---|---|
| | L μl | P μl | L μl | P μl | L μl | P μl | L μl | P μl | L μl | P μl |
| Probe | — | 250 | — | 250 | — | 250 | — | 250 | — | 250 |
| PBS | 250 | — | 250 | — | 250 | — | 250 | — | 250 | — |
| H₂O twice dist. | 50 | 50 | 50 | 50 | — | — | — | — | — | — |
| Phenol 2% | — | — | — | — | 50 | 50 | — | — | — | — |
| Phenol 5% | — | — | — | — | — | — | 50 | 50 | — | — |
| NaNO₂ 0.1M | — | — | — | — | — | — | — | — | 20 | 20 |
| CH₃COOH 0.1M | — | — | — | — | — | — | — | — | 20 | 20 |
| Incub. 15 min, RT | — | — | — | — | — | — | — | — | x | x |
| Tris buffer 0.14 | — | — | — | — | — | — | — | — | 20 | 20 |
| Ab-loaded bead | + | + | + | + | + | + | + | + | + | + |
| Pre-incubation | + | + | + | + | + | + | + | + | + | + |
| Conjugate | 250 | 250 | 250 | 250 | 250 | 250 | 250 | 250 | 250 | 250 |
| Immunol. incubation | + | + | + | + | + | + | + | + | + | + |
| Washing | + | + | + | + | + | + | + | + | + | + |
| Substrate solution | 250 | 250 | 250 | 250 | 250 | 250 | 250 | 250 | 250 | 250 |
| Incubation | + | + | + | + | + | + | + | + | + | + |
| Stop reagent | + | + | + | + | + | + | + | + | + | + |

L = Blank (PBS)
P = Probe

The following results were obtained:

C.1.) Mycobacterium - positive sputum

| Type of treatment | Calculation | |
|---|---|---|
| | OD probe − OD blank | OD probe / OD blank |
| Negative sputum | −0.068 | 0.7 |
| Untreated sputum | 0.153 | 1.6 |
| Sputum + 2% phenol | 1.100 | 6.8 |
| Sputum 100° C. | 0.535 | 3.3 |
| Sputum + NaNO₂ Acetic acid, Tris | 0.464 | 2.7 |

C.2.) Pneumococci - positive sputum

| Type of treatment | Calculation | |
|---|---|---|
| | OD probe − OD blank | OD probe / OD blank |
| Negative sputum | −0.070 | 0.7 |
| Untreated sputum | 1.209 | 7.3 |
| Sputum + 2% phenol | 1.072 | 6.8 |
| Sputum + 5% phenol | 1.081 | 8.1 |
| Sputum 100° C. | 1.110 | 6.8 |
| Sputum + NaNO₂ Acetic acid, Tris | 1.052 | 6.2 |

C.3.) E. coli − positive urine

| Urine | OD probe − OD blank | | | | OD probe / OD blank | | | |
|---|---|---|---|---|---|---|---|---|
| | Type of treatment | | | | Type of treatment | | | |
| | Untreated | 2% Phenol | 5% Phenol | 100° C. | Untreated | 2% Phenol | 5% Phenol | 100° C. |
| U 7224 | 0.021 | 0.124 | 0.215 | 0.164 | 1.5 | 3.7 | 3.6 | 4.5 |
| U 7231 | 0.026 | 0.133 | 0.311 | 0.193 | 1.6 | 3.7 | 4.7 | 4.9 |
| U 7261 | 0.093 | 0.160 | 0.233 | 0.068 | 3.1 | 4.7 | 4.2 | 2.4 |
| U 7282 | 0.101 | 0.197 | 0.347 | 0.181 | 2.6 | 4.0 | 4.9 | 3.9 |
| U 7286 | 0.271 | 0.419 | 0.823 | 0.300 | 5.3 | 7.4 | 10.2 | 5.8 |
| U 7293 | 0.057 | 0.112 | 0.190 | 0.250 | 1.9 | 2.9 | 2.8 | 5.3 |

I claim:

1. A method of treating fluid samples suspected of containing microorganisms having polysaccharide antigens bound therein comprising adding to said sample a 1–10% aqueous phenol solution under conditions and for a time sufficient to cause the dissolution of said antigens into the resulting fluid.

2. The method of claim 1, wherein the microorganisms are selected from the group consisting of bacteria and fungi.

3. The method of claim 2, wherein a 2–5% aqueous phenol solution is used.

4. The method of claim 3 wherein the fluid sample is blood, serum, plasma, urine feces or sputum.

5. The method of claim 4, wherein a 2% aqueous phenol solution is used.

6. The method of claim 5, wherein one part of aqueous phenol solution is used per 5 parts of fluid sample.

7. The method of claim 6, wherein the aqueous phenol solution is allowed to react with said fluid sample for 5–30 minutes.

8. The method of claim 7, wherein the aqueous phenol solution is allowed to react with said fluid sample for about 15 minutes.

9. A method for the immunological detection of microorganisms by detecting polysaccharide antigens bound with said microorganisms comprising adding to a fluid sample suspected of containing said microorganisms a 1–10% aqueous phenol solution to cause the dissolution of said antigens into the resulting fluid, reacting said resulting fluid having said antigens dissolved therein with antibodies which specifically bind to said antigens to form immunological complexes and detecting said complexes.

10. The method of claim 9, wherein the microorganisms are selected from the group consisting of bacteria and fungi.

11. The method of claim 10, wherein the polysaccharide antigens from streptococci, mycobacteria or enterobacteriacae are detected.

12. The method of claim 11, wherein the polysaccharide antigens from *Streptococcus pneumoniae*, *Mycobacterium tuberculosis* or *Escherichia coli* are detected.

* * * * *